United States Patent
Cortez, Jr. et al.

(10) Patent No.: US 9,333,317 B2
(45) Date of Patent: May 10, 2016

(54) SYSTEMS AND METHODS FOR PROVIDING RESPIRATORY THERAPY

(71) Applicant: Vapotherm, Inc., Stevensville, MD (US)

(72) Inventors: Felino V. Cortez, Jr., Bowie, MD (US); William F. Niland, Arnold, MD (US); George McGarrity, Centerville, MD (US)

(73) Assignee: Vapotherm, Inc., Exeter, NH (US)

( * ) Notice: Subject to any disclaimer, the term of this patent is extended or adjusted under 35 U.S.C. 154(b) by 318 days.

(21) Appl. No.: 13/749,162

(22) Filed: Jan. 24, 2013

(65) Prior Publication Data

US 2013/0186395 A1    Jul. 25, 2013

Related U.S. Application Data

(60) Provisional application No. 61/590,045, filed on Jan. 24, 2012.

(51) Int. Cl.
*A61M 16/14*    (2006.01)
*A61M 16/06*    (2006.01)
(Continued)

(52) U.S. Cl.
CPC ........... *A61M 16/14* (2013.01); *A61M 16/0057* (2013.01); *A61M 16/0666* (2013.01); *A61M 16/0672* (2014.02); *A61M 16/0808* (2013.01);
(Continued)

(58) Field of Classification Search
CPC ..... A61M 11/06; A61M 1/00; A61M 1/0062; A61M 1/0076; A61M 11/002; A61M 15/0086; A61M 15/00; A61M 15/08; A61M 16/06; A61M 16/0666; A61M 16/125

USPC ............ 128/200.11–200.24, 203.12, 203.15, 128/203.22; 604/94.01
See application file for complete search history.

(56) References Cited

U.S. PATENT DOCUMENTS 2,485,184 A * 10/1949 Blackman et al. ....... 128/200.22
3,864,326 A    2/1975 Babington
(Continued)

FOREIGN PATENT DOCUMENTS

RU    2009111135 A    10/2010
RU    2432190 C2    10/2011

OTHER PUBLICATIONS

International Search Report dated Oct. 19, 2010, application No. PCT/US2010/023331.
(Continued)

*Primary Examiner* — Annette Dixon
(74) *Attorney, Agent, or Firm* — Ropes & Gray LLP

(57) ABSTRACT

A system for respiratory therapy that includes a nebulizer, an adaptor, and a nasal cannula. The nebulizer is operable to generate an aerosolized medicament and pass the aerosolized medicament through a nebulizer outlet port. The adaptor has a nebulizer coupling port configured to be coupled to the nebulizer outlet port. The nasal cannula is configured to provide a flow of breathing gas from a breathing gas source to the patient. The nasal cannula includes at least one nasal prong and an attachment device positioned adjacent the at least one nasal prong. The attachment device is configured to secure the adaptor outlet port adjacent an outlet of the nasal prong. A method for respiratory therapy includes securing a nasal cannula to the patient, attaching an adaptor to the nasal cannula, generating an aerosolized medicament, transferring the aerosolized medicament into the adaptor, and providing a flow of breathing gas to the patient.

39 Claims, 5 Drawing Sheets

Figure 1:
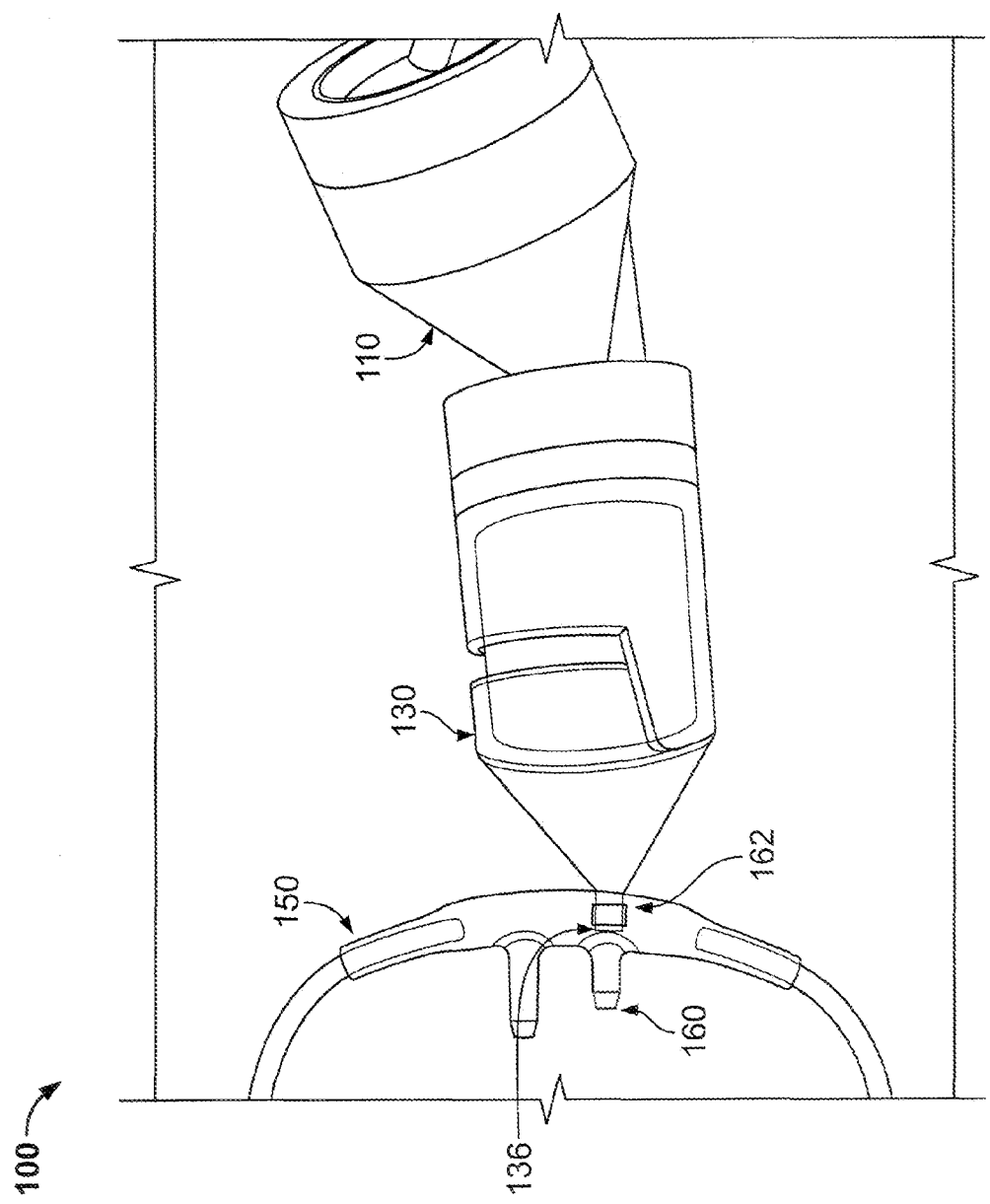

(51) Int. Cl.
*A61M 16/08* (2006.01)
*A61M 16/00* (2006.01)

(52) U.S. Cl.
CPC ....... *A61M 16/0816* (2013.01); *A61M 16/0875* (2013.01)

(56) References Cited

U.S. PATENT DOCUMENTS

| | | | |
|---|---|---|---|
| 4,177,945 A | | 12/1979 | Schwartz et al. |
| 4,805,609 A | * | 2/1989 | Roberts et al. ........... 128/200.21 |
| 4,819,625 A | | 4/1989 | Howe |
| 4,832,012 A | | 5/1989 | Raabe et al. |
| 4,911,157 A | | 3/1990 | Miller |
| 5,226,411 A | | 7/1993 | Levine |
| 5,335,656 A | * | 8/1994 | Bowe et al. ............. 128/207.18 |
| 5,461,695 A | | 10/1995 | Knoch |
| 5,584,285 A | * | 12/1996 | Salter et al. ............. 128/200.21 |
| 5,630,409 A | | 5/1997 | Bono et al. |
| 8,561,607 B2 | * | 10/2013 | Cortez et al. ............. 128/203.12 |
| 2004/0237178 A1 | | 12/2004 | Landeros |
| 2005/0229927 A1 | | 10/2005 | Fink et al. |
| 2005/0229928 A1 | | 10/2005 | Ivri et al. |
| 2006/0078506 A1 | | 4/2006 | Niven et al. |
| 2008/0000470 A1 | | 1/2008 | Minocchieri et al. |
| 2010/0089395 A1 | | 4/2010 | Power et al. |
| 2010/0258114 A1 | | 10/2010 | Cortez, Jr. et al. |
| 2011/0000487 A1 | | 1/2011 | Moa et al. |

OTHER PUBLICATIONS

International Search Report dated Apr. 21, 2013, application No. PCT/US2013/022692.
International Search Report and Written Opinion for PCT/2013/022692 dated Jul. 29, 2014.
Supplementary European Search Report for PCT/US2013/022692 dated Jul. 8, 2015.

* cited by examiner

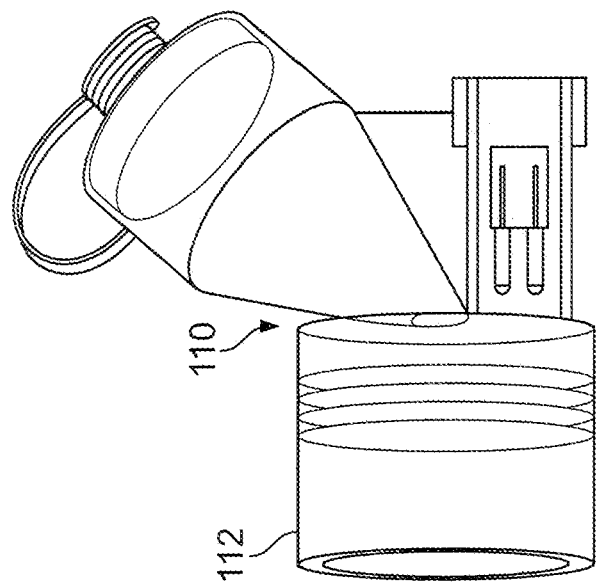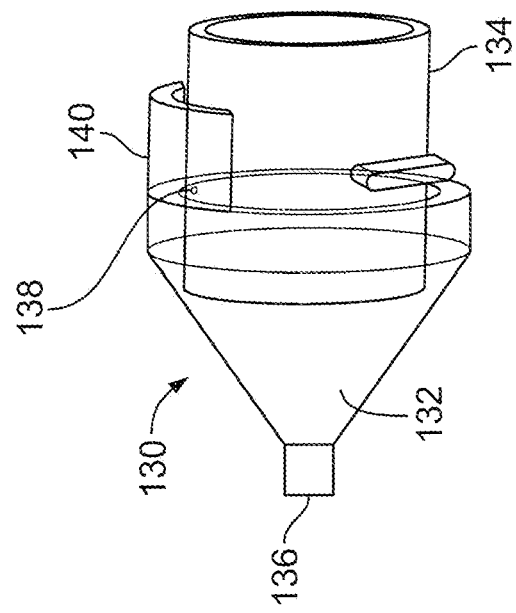
FIG. 2

200

210 — Secure nasal cannula to patient

220 — Attach adaptor to nasal cannula such that adaptor outlet port is positioned adjacent outlet of nasal prong 230 — Generate aerosolized medicament with nebulizer 240 — Transfer aerosolized medicament into adaptor 250 — Provide flow of breathing gas to patient through nasal prong such that aerosolized medicament is drawn outward from adaptor

FIG. 5

SYSTEMS AND METHODS FOR PROVIDING RESPIRATORY THERAPY

CROSS-REFERENCE TO RELATED APPLICATIONS

This application claims priority to U.S. Patent Application No. 61/590,045, filed Jan. 24, 2012, entitled "SYSTEMS AND METHODS FOR PROVIDING RESPIRATORY THERAPY", the contents of which are incorporated herein by reference.

FIELD OF THE INVENTION

The present invention relates generally to respiratory therapy, and more particularly to systems and methods for use in providing respiratory therapy.

BACKGROUND OF THE INVENTION

Patients with respiratory ailments may be administered supplemental breathing gases, such as oxygen, for example, to aid in respiration. These breathing gases are typically provided from a breathing gas supply, such as an oxygen tank. A delivery device, such as a nasal cannula, may be coupled to the breathing gas supply and inserted into a patient's nasal passages for delivery of the breathing gas to the patient for inhalation.

Separately, respiratory medications may be administered through inhalation directly to the patient's lungs. These respiratory medications may be aerosolized by a nebulizer in order to generate small particles of the medication, which facilitate distribution throughout the patient's lungs during inhalation. Conventional nebulizers draw liquid medicament from a liquid reservoir to form a nebulized aerosol for inhalation.

SUMMARY OF THE INVENTION

Aspects of the present invention are directed to systems and methods for respiratory therapy.

In accordance with one aspect of the present invention, a system for providing respiratory therapy to a patient is disclosed. The system comprises a nebulizer, an adaptor, and a nasal cannula. The nebulizer has a nebulizer outlet port. The nebulizer is operable to generate an aerosolized medicament and pass the aerosolized medicament through the nebulizer outlet port. The adaptor has an adaptor body, a nebulizer coupling port, and an adaptor outlet port. The nebulizer coupling port of the adaptor is configured to be coupled to the nebulizer outlet port of the nebulizer. The nasal cannula is configured to provide a flow of breathing gas from a breathing gas source to the patient. The nasal cannula comprises at least one nasal prong and an attachment device positioned adjacent the at least one nasal prong. The attachment device is configured to secure the adaptor outlet port adjacent an outlet of the nasal prong.

In accordance with another aspect of the present invention, a method of providing respiratory therapy to a patient is disclosed. The method comprises securing a nasal cannula to the patient, attaching an adaptor to the nasal cannula using an attachment device such that an adaptor outlet port of the adaptor is positioned adjacent an outlet of a nasal prong of the nasal cannula, generating an aerosolized medicament with a nebulizer, transferring the aerosolized medicament into the adaptor through a nebulizer coupling port of the adaptor, and providing a flow of breathing gas to the patient through the nasal prong such that the aerosolized medicament is drawn outward from the adaptor through the adaptor outlet port and inhaled by the patient with the flow of breathing gas.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. According to common practice, the various features of the drawings are not drawn to scale, unless otherwise indicated. On the contrary, the dimensions of the various features may be expanded or reduced for clarity. Included in the drawings are the following figures:

FIG. 1 is an image illustrating an exemplary system for providing respiratory therapy in accordance with aspects of the present invention;

FIG. 2 is an image illustrating an exemplary adaptor of the system of FIG. 1;

FIGS. 3 and 4 are images illustrating an exemplary nasal cannula of the system of FIG. 1;

FIG. 5 is a flowchart illustrating an exemplary method for providing respiratory therapy in accordance with aspects of the present invention;

FIG. 6 is an image illustrating another exemplary system for providing respiratory therapy in accordance with aspects of the present invention.

DETAILED DESCRIPTION OF THE INVENTION

Embodiments of the present invention are directed to systems and methods for providing respiratory therapy to a patient. These exemplary embodiments may be particularly suitable for providing an aerosolized medicament to a patient via a breathing device, such as a nasal cannula. Suitable medicaments for use with the disclosed systems will be known to one of ordinary skill in the art. Additionally, while the exemplary embodiments are described herein for use in conjunction with a nasal cannula, it will be understood that other breathing devices may be used without departing from the scope of the invention.

As a general overview, the disclosed embodiments of the present invention are usable to provide aerosolized medicament along with a flow of breathing gas to a patient. The embodiments operate by using the slipstream effect to entrain the aerosolized medicament in the flow of breathing gas. As the flow of breathing gas leaves a breathing device (such as a nasal cannula) for inhalation by the patient, the aerosolized medicament is drawn into the breathing gas slipstream, and thereby inhaled by the patient along with the breathing gas.

Referring now to the drawings, FIGS. 1-4 illustrate an exemplary system 100 for providing respiratory therapy to a patient in accordance with aspects of the present invention. Generally, system 100 includes a nebulizer 110, an adaptor 130, and a nasal cannula 150. Additional details of system 100 will be described herein.

Nebulizer 110 is operable to generate an aerosolized medicament. Nebulizer 110 includes an aerosol generator (not shown) that aerosolizes a medicament contained within nebulizer 110. As shown in FIG. 2, nebulizer 110 also includes a nebulizer outlet port 112 at the bottom of nebulizer 110. For example, nebulizer 110 may use an electrical signal to draw fluid into a vibratory aerosolization element (not shown), to generate an aerosol mist in the form of a low velocity cloud of aerosolized medicament. The cloud of aerosolized medicament exits nebulizer 110 by passing through nebulizer outlet port 112. In an exemplary embodiment, nebulizer 110 is the AERONEB® Solo nebulizer, available from Aerogen, Ltd of Galway, Ireland. However, essentially any conventional nebulizer may be used (with corresponding modifications to the size of the nebulizer coupling port of the adaptor), as would be understood by one of ordinary skill in the art from the description herein.

Adaptor 130 is couplable to nebulizer 110. As shown in FIG. 2, adaptor 130 has an adaptor body 132 defining a mixing chamber. Adaptor 130 includes a nebulizer coupling port 134 and an adaptor outlet port 136. Ports 134 and 136 each open into the mixing chamber defined by adaptor body 132. Nebulizer coupling port 134 of adaptor 130 is configured to be coupled to the outlet port 112 of nebulizer 110 (e.g., by friction fit) in order to receive the cloud of aerosolized medicament. Accordingly, the size of nebulizer coupling port 134 may be selected based on the nebulizer 110 used with system 100. The cloud of aerosolized medicament may then pass into the adaptor body 132. Suitable materials for forming adaptor 130 will be known to one of ordinary skill in the art from the description herein.

Adaptor 130 may desirably have an adaptor outlet port 136 that is limited in size (e.g., less than 1 mm in diameter). Adapter outlet port 136 may have a cross-sectional area less than the cross-sectional area of nebulizer coupling port 134. Adaptor outlet port 136 may be configured to be attached to a corresponding attachment device of nasal cannula 150, as will be described in greater detail below.

In an exemplary embodiment, adaptor body 132 is an approximately cone-shaped body between nebulizer coupling port 134 and adaptor outlet port 136, as shown in FIG. 2. The cone-shaped body may further include a cylindrical portion extending therefrom for attachment to nebulizer outlet port 112. Adaptor body 132 is shaped such that adaptor outlet port 136 has a cross-sectional area less than that of nebulizer coupling port 134. This feature may be desirable in order to precisely regulate the flow of aerosolized medicament from adaptor 130.

Adaptor 130 may comprise a vent hole 138. Vent hole 138 is positioned between nebulizer coupling port 134 and adaptor outlet port 136. Vent hole 138 enables venting of pressure that may build up within adaptor 130 during use of system 100. This may be desirable when the flow of aerosolized medicament from nebulizer 110 into adaptor 130 is in excess of the flow of aerosolized medicament out of adaptor outlet port 136. In this embodiment, adaptor 130 may further comprise a shielding portion 140. Shielding portion 140 is positioned to prevent obstruction of vent hole 138 so that adaptor 130 can function normally during use. Shielding portion 140 can be integrally formed with adaptor body 132, as shown in FIG. 2.

Adaptor 130 may desirably be removably attached to nebulizer 110, as shown in FIG. 2. In an exemplary embodiment, nebulizer coupling port 134 is configured to be slidably received within nebulizer outlet port 112. Removably attaching adaptor 130 to nebulizer 110 may enable multiple adaptors 130 having differently sized adaptor outlet ports 136 to be used with system 100. This may be desirable to change the amount of aerosolized medicament provided during use of system 100.

While adaptor 130 is illustrated as having a single adaptor outlet port 136, it will be understood by one of ordinary skill in the art that the invention is not so limited. Adaptor 130 may be designed to include a pair of spaced apart adapter outlet ports 136. The spacing between the pair of adaptor outlet ports 136 may be selected to correspond to the spacing between nasal prongs of an associated nasal cannula, so that the aerosolized medicament may be provided through both nares of the patient (instead of via a single nare).

Figure 3:
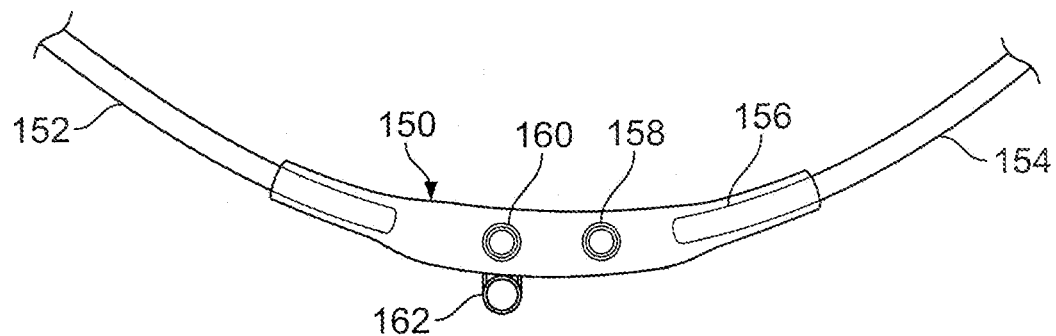
Figure 4:
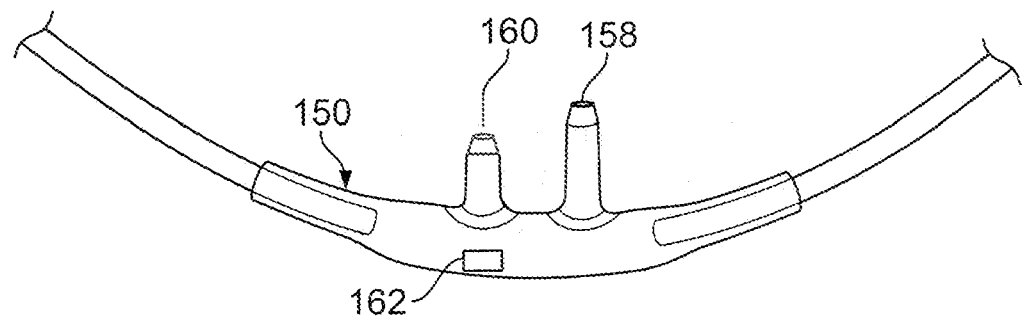

Nasal cannula 150 is configured to provide a flow of breathing gas from a breathing gas source to the patient. In an exemplary embodiment, nasal cannula 150 comprises a first supply tube 152, a second supply tube 154, and a cannula body 156, as shown in FIGS. 3 and 4. Supply tubes 152 and 154 are elongated, hollow lumens. Supply tubes 152 and 154 may be connected to a connector (not shown) in order to receive breathing gas from a breathing gas source. Thereby, supply tubes 152 and 154 enable fluid communication between the breathing gas source and cannula body 156.

Cannula body 156 is coupled to the ends of supply tubes 152 and 154. As shown in FIGS. 3 and 4, cannula body 156 includes nasal prongs 158 and 160 extending from cannula body 156. When nasal cannula 150 is secured to the patient, nasal prongs 158 and 160 are positioned within respective nares of the patient. Nasal prongs 158 and 160 provide the flow of breathing gas received from supply tubes 152 and 154 to the patient.

Nasal cannula 150 may further comprise an attachment device 162. As shown in FIGS. 3 and 4, attachment device 162 is provided on cannula body 156 and positioned adjacent one of the nasal prongs 160. In one embodiment, attachment device 162 is positioned directly adjacent the base of nasal prong 160.

Attachment device 162 is configured to secure adaptor outlet port 136 adjacent an outlet of nasal prong 160. In particular, attachment device 162 may position adaptor outlet port 136 substantially within or directly below a nare of the patient when nasal cannula 150 is secured to the patient, on an anterior surface of cannula body 156. In this way, the aerosolized medicament from nebulizer 110 may be provided to the patient along with the flow of breathing gas from nasal cannula 150 using the slipstream effect. When adaptor outlet port 136 is secured by attachment device 162, the aerosolized medicament may desirably be drawn into the breathing gas slipstream, and thereby inhaled by the patient along with the breathing gas. It may be desirably that adaptor outlet port 136 be positioned outside of the nare of the patient (i.e. directly below the nare), in order to avoid obstructing the patient's nare during use.

In one embodiment, the above-described slipstreaming effect may be increased through the use of a nasal cannula 150 having a shorter nasal prong. As shown in FIGS. 3 and 4, nasal cannula 150 includes one nasal prong 160 that is shorter than the other nasal prong 158, e.g., approximately half as long. A suitable length for shorter nasal prong 160 may be between approximately 3-4 mm for infant and pediatric patients, and between approximately 6-7 mm for adult patients. Attachment device 162 is positioned directly adjacent the base of the shorter nasal prong 160. The use of a nasal cannula 150 having this design enables system 100 to have one nasal prong 158 optimized for the delivery of breathing gas and one nasal prong 160 optimized for slipstreaming aerosolized medicament.

Attachment device 162 may comprise a loop configured to receive a portion of adaptor 130 therethrough, as shown in FIGS. 1 and 3. Correspondingly, adaptor 130 may comprise a protrusion adapted to be received within the attachment device 162 of the nasal cannula 150. As shown in FIGS. 1 and 2, adaptor 130 comprises a protrusion (defining adaptor outlet port 136) which may be received in the loop during use of system 100.

While attachment device 162 is shown in FIG. 3 as a loop, it will be understood by one of ordinary skill in the art that the invention is not so limited. Attachment device 162 may comprise any structure adapted to secure a portion of adaptor 130 to nasal cannula 150 in the proper position (i.e., in a position which allows slipstreaming of the aerosolized medicament within the flow of breathing gas from nasal cannula 150). Suitable structures include, for example, U-clips, hook-and-loop fasteners, or magnets. Other suitable attachment devices 162 will be known to one of ordinary skill from the description herein.

In an alternative embodiment, nasal cannula 150 does not include an attachment device, and/or adaptor 130 does not include a protrusion for coupling to the attachment device. In this embodiment, adaptor 130 may be held in place during use. Adaptor body 132 may comprise one or more structures (such as wings, grips, depressions, or other features) that facilitate proper positioning and holding of adaptor 130 by the user. Suitable structures for assisting the user in holding or positioning adaptor 130 will be known to one of ordinary skill in the art from the description herein.

System 100 is not limited to the above components, but may include alternative or additional components, as would be understood by one of ordinary skill in the art.

For one example, system 100 may further comprise a source of breathing gas. The source of breathing gas provides breathing gas for inhalation by a user of system. The source may desirably generate heated and humidified breathing gas. In an exemplary embodiment, the breathing gas source is the Vapotherm 2000i, the Vapotherm Precision Flow, the Vapotherm Flowrest System, or the Vapotherm Careflow system provided by Vapotherm, Inc of Stevensville, Md., USA. Other suitable breathing gas sources will be known to one of ordinary skill in the art from the description herein. The source of breathing gas may be coupled to supply tubes 152 and 154 of nasal cannula 150, in order to provide the breathing gas to the patient.

FIG. 5 is a flowchart illustrating an exemplary method 200 for providing respiratory therapy in accordance with aspects of the present invention. Method 200 may be implemented using the exemplary system 100 described above. Generally, method 200 includes securing a nasal cannula to the patient, attaching an adaptor to the nasal cannula, generating an aerosolized medicament, transferring the aerosolized medicament to the adaptor, and providing a flow of breathing gas to the patient. Additional details of method 200 will be described herein with reference to system 100.

In step 210, a nasal cannula is secured to the patient. In an exemplary embodiment, nasal cannula 150 is secured to the patient. When nasal cannula 150 is secured to the patient, nasal prongs 158 and 160 are positioned within respective nares of the patient.

In step 220, an adaptor is attached to the nasal cannula. In an exemplary embodiment, adaptor 130 is attached to nasal cannula 150 using attachment device 162. Adaptor 130 is attached to nasal cannula 150 such that adaptor outlet port 136 is positioned adjacent an outlet of nasal prong 160 of nasal cannula 150. In particular, attachment device 162 may position adaptor outlet port 136 substantially within or directly below a nare of the patient when nasal cannula 150 is secured to the patient in step 210.

As set forth above, attachment device 162 may comprise a loop, and adaptor 130 may comprise a protrusion adapted to be received within the loop. Accordingly, step 220 may comprise positioning a protrusion of the adaptor 130 within the loop.

Additionally, as set forth above, nasal cannula 150 may include one nasal prong 160 that is shorter than the other nasal prong 158. Accordingly, step 220 may comprise attaching adaptor 130 to nasal cannula 150 such that adaptor outlet port 136 is positioned adjacent an outlet of the shorter nasal prong 160, in order to optimize slipstreaming of the aerosolized medicament.

In step 230, an aerosolized medicament is generated. In an exemplary embodiment, nebulizer 110 generates an aerosolized medicament, substantially as described above.

In step 240, the aerosolized medicament is transferred into the adaptor. In an exemplary embodiment, the aerosolized medicament generated by nebulizer 110 passes out of nebulizer 110 through the nebulizer output port 112. Adaptor 130 is coupled to nebulizer 110 such that the aerosolized medicament passes in through nebulizer coupling port 134 into adaptor body 132 of adaptor 130.

In step 250, a flow of breathing gas is provided to the patient. In an exemplary embodiment, a flow of breathing gas is provided to the patient through nasal prongs 158 and 160 of nasal cannula 150. Due to the positioning of adaptor outlet port 136 within attachment device 162, the flow of breathing gas causes the aerosolized medicament within adaptor 130 to be drawn outward from adaptor 130 through adaptor outlet port 136 and inhaled by the patient with the flow of breathing gas.

Thereby, step 250 uses the slipstream effect to entrain the aerosolized medicament in the flow of breathing gas. As set forth above, the slipstreaming effect may be enhanced where adaptor outlet port 136 has a cross-sectional area less than that of nebulizer coupling port 134.

Method 200 is not limited to the above steps, but may include alternative or additional steps, as would be understood by one of ordinary skill in the art.

For one example, adaptor 130 may be removably attachable to nebulizer 110, as described above with respect to system 100. Accordingly, method 200 may include the step of removably attaching adaptor 130 to nebulizer 110.

For another example, adaptor 130 may comprise a vent hole 138 for enabling release of pressure from within adaptor 130. Accordingly, method 200 may include the step of venting a portion of the aerosolized medicament from adaptor 130 using vent hole 138.

For yet another example, adaptor 130 may comprise a drainage port, as described in greater detail below. Accordingly, method 200 may include the step of draining a liquid medicament from adaptor 130 via the drainage port. Where the system further comprises a syringe, the draining step may comprise withdrawing the liquid medicament from the adaptor with a syringe.

Figure 6:
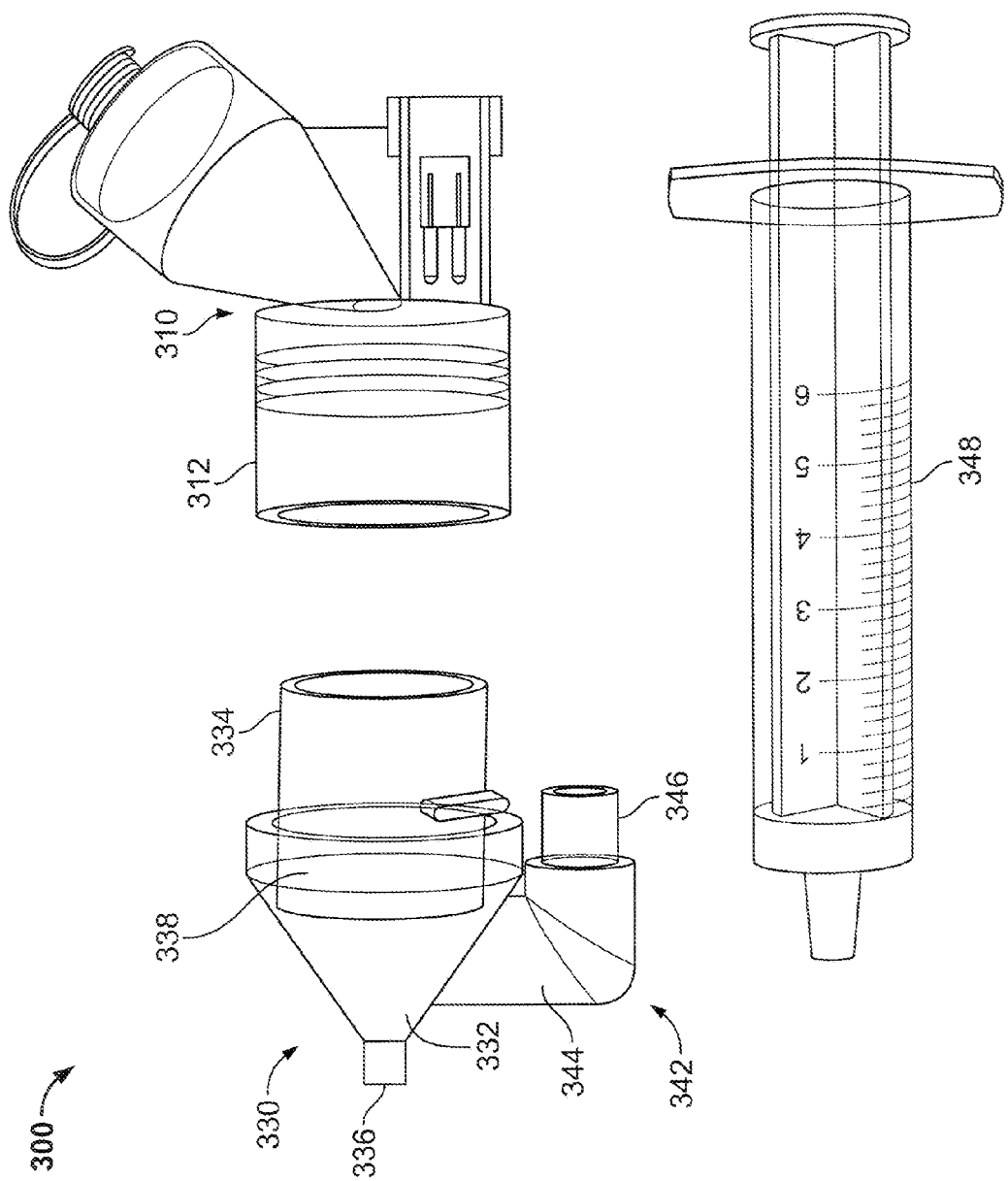

FIG. 6 illustrates another exemplary system 300 for providing respiratory therapy to a patient in accordance with aspects of the present invention. Generally, system 300 includes a nebulizer 310 and an adaptor 330. Additional details of system 300 will be described herein.

Nebulizer 310 is operable to generate an aerosolized medicament. As shown in FIG. 6, nebulizer 310 includes a nebulizer outlet port 312 at the bottom of nebulizer 310. Nebulizer 310 may be a nebulizer substantially as described above with respect to nebulizer 110.

Adaptor 330 is couplable to nebulizer 310. As shown in FIG. 6, adaptor 330 has an adaptor body 332 defining a mixing chamber. Adaptor 330 includes a nebulizer coupling port 334 and an adaptor outlet port 336. Ports 334 and 336 each open into the mixing chamber defined by adaptor body 332. Adaptor 330 may include any of the features described above with respect to adaptor 130. Nebulizer coupling port 334 of adaptor 330 is configured to be coupled to the outlet port 312 of nebulizer 310 (e.g., by friction fit) in order to receive the cloud of aerosolized medicament. Adaptor 330 may include any of the features described above with respect to adaptor 130.

Adaptor 330 further comprises a drainage port 342. Drainage port 342 enables drainage of liquid medicament from adaptor body 332. In an exemplary embodiment, adaptor 330 may accumulate excess liquid medicament within adaptor body 332 during use. This excess liquid medicament may interfere with regular operation of system 300. Accordingly, adaptor 330 is provide with drainage port 342 to enable drainage of this excess liquid medicament, and regular operation of system 300.

In an exemplary embodiment, drainage port 342 comprises an elbow-shaped lumen extending outwardly from adaptor body 332, as shown in FIG. 6. The elbow-shaped lumen has a first end 344 affixed to adaptor body 332 and a second end 346 distal from adaptor body 332. Distal end 346 extends in the direction of nebulizer coupling port 334 and away from adaptor outlet port 336. This enables coupling distal end 346 to a syringe 348 without interfering with use of system 300. While drainage port 342 is illustrated as an elbow-shaped lumen, it will be understood by one of ordinary skill in the art that it is not so limited. Drainage port 342 could for example be a straight lumen, or could have any other desirable shape. Additionally, while drainage port 342 is illustrated as substantially rigid, it will be understood by one of ordinary skill in the art that drainage port 342 could be formed from a flexible material.

As shown in FIG. 6, system 300 further comprises syringe 348. Syringe 348 is adapted to be coupled to distal end 346 of drainage port 342. Syringe 348 is configured to withdrawn liquid medicament from adaptor body 332 via drainage port 342. For example, syringe 348 may include a plunger which can be pulled outward by a user of system 300 in order to withdraw the liquid medicament. The liquid withdrawn by syringe 348 may additionally be reused to generate aerosolized medicament with nebulizer 310. Suitable syringes for use as syringe 348 will be known to one of ordinary skill in the art from the description herein. It will be understood by one of ordinary skill in the art that other objects may be used to facilitate withdrawing liquid medicament from adaptor body 332 without departing from the invention.

Adaptor body 332 may be an approximately cone-shaped body between nebulizer coupling port 334 and adaptor outlet port 336, as shown in FIG. 6. The cone-shaped body may further include a cylindrical portion extending therefrom for attachment to nebulizer outlet port 312. In this embodiment, drainage port 342 is formed in the cone-shaped body. Preferably, drainage port 342 is formed on a lower portion of adaptor body 332, to enable gravity to assist in drainage of adaptor body 332.

Adaptor 330 may comprise a vent hole 338 positioned between nebulizer coupling port 334 and adaptor outlet port 336. Drainage port 342 may be formed on an opposite side of adaptor body from vent hole 338.

System 300 may further include a nasal cannula configured to provide a flow of breathing gas from a breathing gas source to a patient. In an exemplary embodiment, system 300 includes a nasal cannula substantially as described above with respect to nasal cannula 350.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A system for providing respiratory therapy to a patient comprising:
   a nebulizer having a nebulizer outlet port, the nebulizer operable to generate an aerosolized medicament and pass the aerosolized medicament through the nebulizer outlet port;
   an adaptor having an adaptor body, a nebulizer coupling port, and an adaptor outlet port, the nebulizer coupling port of the adaptor configured to be coupled to the nebulizer outlet port of the nebulizer; and
   a nasal cannula configured to provide a flow of breathing gas from a breathing gas source to the patient, the nasal cannula comprising at least one nasal prong and an attachment device positioned adjacent the at least one nasal prong, the attachment device configured to secure the adaptor outlet port adjacent to an outlet of the at least one nasal prong along the nasal cannula;
   wherein the at least one nasal prong has a first longitudinal axis and wherein the adaptor outlet port has a second longitudinal axis, wherein the first longitudinal axis is parallel to and laterally offset from the second longitudinal axis.

2. The system of claim 1, wherein the adaptor outlet port has a cross-sectional area less than the nebulizer coupling port.

3. The system of claim 2, wherein the adaptor body comprises an approximately cone-shaped body extending between the nebulizer coupling port and the adaptor outlet port, the cone-shaped body oriented such that the adaptor outlet port has the cross-sectional area less than the nebulizer coupling port.

4. The system of claim 1, wherein the adaptor outlet port comprises a protrusion adapted to be received within the attachment device of the nasal cannula.

5. The system of claim 1, wherein the adaptor body comprises a vent hole positioned between the nebulizer coupling port and the adaptor outlet port, the vent hole enabling venting of pressure from the adaptor.

6. The system of claim 5, wherein the adaptor further comprises a shielding portion positioned adjacent the vent hole, the shielding portion disposed to prevent obstruction of the vent hole.

7. The system of claim 1, wherein the adaptor is removably attached to the nebulizer.

8. The system of claim 7, wherein the nebulizer coupling port is configured to be slidably received within the nebulizer outlet port.

9. The system of claim 1, wherein the at least one nasal prong comprises a pair of nasal prongs, and the attachment device is positioned directly adjacent a base of one of the pair of nasal prongs.

10. The system of claim 9, wherein the one of the pair of nasal prongs is shorter than another one of the pair of nasal prongs.

11. The system of claim 1, wherein the attachment device is configured to position the adaptor outlet port directly below a nare of the patient when the nasal cannula is secured to the patient.

12. The system of claim 1, wherein the attachment device comprises a loop configured to receive a portion of the adaptor therethrough.

13. The system of claim 1, wherein the nasal cannula further comprises a nasal cannula body and tubing connected to the nasal cannula body for supplying breathing gas to the nasal cannula body.

14. A method of providing respiratory therapy to a patient, the method comprising:
securing a nasal cannula to the patient;
attaching an adaptor to the nasal cannula using an attachment device such that an adaptor outlet port of the adaptor is positioned adjacent to an outlet of a nasal prong along the nasal cannula;
generating an aerosolized medicament with a nebulizer;
transferring the aerosolized medicament into the adaptor through a nebulizer coupling port of the adaptor; and
providing a flow of breathing gas to the patient through the nasal prong such that the aerosolized medicament is drawn outward from the adaptor through the adaptor outlet port for inhalation by the patient with the flow of breathing gas;
wherein the nasal prong has a first longitudinal axis and wherein the adaptor outlet port has a second longitudinal axis, wherein the first longitudinal axis is laterally offset from the second longitudinal axis.

15. The method of claim 14, wherein the providing step comprises drawing the aerosolized medicament outward from the adaptor through the adaptor outlet port having a cross-sectional area less than the nebulizer coupling port.

16. The method of claim 14, wherein the attachment device comprises a loop, and the step of attaching comprises:
positioning a protrusion of the adaptor within the loop.

17. The method of claim 14, further comprising the step of:
removably attaching the adaptor to the nebulizer.

18. The method of claim 17, further comprising the step of:
venting a portion of the aerosolized medicament from the adaptor using a vent hole provided in the adaptor.

19. The method of claim 14, wherein the nasal cannula comprises another nasal prong, with the nasal prong shorter than the other nasal prong, and wherein the attaching step comprises attaching the adaptor to the nasal cannula such that the adaptor outlet port is positioned adjacent an outlet of the nasal prong.

20. The method of claim 14, wherein the securing step comprises securing the nasal cannula to the patient such that the adaptor outlet port is positioned substantially within or directly below a nare of the patient.

21. The method of claim 14, further comprising the step of:
draining a liquid medicament from the adaptor via a drainage port.

22. The method of claim 14, wherein the draining step comprises withdrawing the liquid medicament from the adaptor with a syringe.

23. A system for providing respiratory therapy to a patient comprising:
a nebulizer having a nebulizer outlet port, the nebulizer operable to generate an aerosolized medicament and pass the aerosolized medicament through the nebulizer outlet port;
an adaptor having an adaptor body, a nebulizer coupling port, an adaptor outlet port, and a drainage port, the nebulizer coupling port of the adaptor configured to be coupled to the nebulizer outlet port of the nebulizer, the drainage port enabling drainage of a liquid medicament from the adaptor body; and
a nasal cannula configured to provide a flow of breathing gas from a breathing gas source to the patient, the nasal cannula comprising at least one nasal prong and an attachment device positioned adjacent the at least one nasal prong, the attachment device configured to secure the adaptor outlet port adjacent to an outlet of the nasal prong along the nasal cannula;
wherein the at least one nasal prong has a first longitudinal axis and wherein the adaptor outlet port has a second longitudinal axis, wherein the first longitudinal axis is laterally offset from the second longitudinal axis.

24. The system of claim 23, wherein the adaptor outlet port has a cross-sectional area less than the nebulizer coupling port.

25. The system of claim 24, wherein the adaptor body comprises an approximately cone-shaped body extending between the nebulizer coupling port and the adaptor outlet port, the cone-shaped body oriented such that the adaptor outlet port has the cross-sectional area less than the nebulizer coupling port.

26. The system of claim 25, wherein the drainage port is formed in the cone-shaped body.

27. The system of claim 23, wherein the adaptor outlet port comprises a protrusion adapted to be received within the attachment device of the nasal cannula.

28. The system of claim 23, wherein the adaptor body comprises a vent hole positioned between the nebulizer coupling port and the adaptor outlet port, the vent hole enabling venting of pressure from the adaptor.

29. The system of claim 28, wherein the adaptor further comprises a shielding portion positioned adjacent the vent hole, the shielding portion disposed to prevent obstruction of the vent hole.

30. The system of claim 28, wherein the drainage port is formed opposite the vent hole in the adaptor body.

31. The system of claim 23, wherein the adaptor is removably attached to the nebulizer.

32. The system of claim 31, wherein the nebulizer coupling port is configured to be slidably received within the nebulizer outlet port.

33. The system of claim 23, wherein the at least one nasal prong comprises a pair of nasal prongs, and the attachment device is positioned directly adjacent a base of one of the pair of nasal prongs.

34. The system of claim 33, wherein the one of the pair of nasal prongs is shorter than the other one of the pair of nasal prongs.

35. The system of claim 23, wherein the attachment device is configured to position the adaptor outlet port directly below a nare of the patient when the nasal cannula is secured to the patient.

36. The system of claim 23, wherein the attachment device comprises a loop configured to receive a portion of the adaptor therethrough.

37. The system of claim 23, wherein the drainage port comprises an elbow-shaped lumen extending outwardly from the adaptor body.

38. The system of claim 37, wherein an end of the elbow-shaped lumen distal the adaptor body extends in the direction of the nebulizer coupling port.

39. The system of claim 38, further comprising a syringe adapted to be coupled to the end of the elbow-shaped lumen distal the adaptor body, the syringe configured to withdraw the liquid medicament from the adaptor body.

* * * * *